United States Patent [19]

Uschold

[11] 4,420,638

[45] Dec. 13, 1983

[54] FLUORINATED ETHER-KETONES

[75] Inventor: Ronald E. Uschold, West Chester, Pa.

[73] Assignee: E. I. Du Pont de Nemours and Company, Wilmington, Del.

[21] Appl. No.: 353,816

[22] Filed: Mar. 2, 1982

[51] Int. Cl.$^3$ .................. C07C 49/175; C07C 49/227
[52] U.S. Cl. .................................... 568/415; 568/308; 568/376; 568/416
[58] Field of Search ............... 568/415, 416, 419, 308, 568/376, 418

[56] References Cited

U.S. PATENT DOCUMENTS

| | | |
|---|---|---|
| 2,925,424 | 2/1960 | Simmons . |
| 3,274,239 | 9/1966 | Selman . |
| 3,311,658 | 3/1967 | Warnell ............................ 260/544 |
| 3,351,619 | 11/1967 | Warnell . |
| 3,865,845 | 2/1975 | Resnick . |
| 3,978,030 | 8/1976 | Resnick ............................ 526/247 |
| 4,035,565 | 7/1977 | Apotheker et al. ............... 526/249 |
| 4,131,740 | 12/1978 | England ............................ 560/180 |
| 4,138,426 | 2/1979 | England ............................ 560/184 |
| 4,214,060 | 7/1980 | Apotheker et al. ............... 525/387 |
| 4,271,275 | 6/1981 | Maclachlan ........................ 525/112 |
| 4,275,226 | 6/1981 | Yamabe et al. .................... 560/183 |

OTHER PUBLICATIONS

Fainberg, Arnold H. et al., *J. Am. Chemical Society*, vol. 79 (1957) pp. 4170–4174.

Hudlicky, Milos *Chemistry of Organic Fluorine Compounds*, (1962) MacMillan, Publ. pp. 247 and 271.

Haszeldine, R. N. *J. Chemical Society* (1951) pp. 584–587.

*Primary Examiner*—Natalie Trousof
*Assistant Examiner*—L. Hendriksen

[57] ABSTRACT

Chlorodifluorovinyloxyperfluoroalkyleneoxyalkyl trifluoromethyl ketones and acyl fluorides; chlorodifluorovinyloxyperfluoroalkyleneoxyethylenes; substituted fluoroalkoxyperfluoroalkyleneoxyalkyl trifluoromethyl ketones and acyl fluorides; substituted fluoroalkoxyperfluoroalkyleneoxyethylenes; processes for their preparation and for the preparation of perfluorovinyloxyalkyleneoxyalkyl bromides; and copolymers of derivatives of the aforesaid vinyl compounds.

5 Claims, No Drawings

FLUORINATED ETHER-KETONES

DESCRIPTION

1. Technical Field

This invention relates to perfluoro[ω-(1,2-dihalotrifluoroethoxy)carboxylates], to functionally-substituted polyethers produced therefrom, including fluorinated olefins, and to polymers of the fluorinated olefins.

2. Background Art

U.S. Pat. Nos. 4,131,740 and 4,138,426 disclose fluorinated compounds, including olefins of the formula $YCF_2CF_2O[CF(CF_3)CF_2O]_pCF=CF_2$ wherein p is 0 to 5 and Y is cyano or carboxyl, or ester or alkali metal, ammonium or quaternary ammonium salt thereof. Similar compounds wherein, using the aforesaid formula, Y is chloro, bromo or iodo, are known from U.S. Pat. Nos. 3,351,619 and 4,275,226. The olefins of the aforesaid formula generally can be prepared by pyrolyzing the corresponding acid fluoride over a basic salt.

The addition of chlorine, bromine or alcohols to fluoroolefins is known, for example, from Fainberg and Miller, *J. Am. Chem. Soc.*, 79, 4170 (1957); "Chemistry of Organic Fluorine Compounds," Hudlicky, The MacMillan Company, New York, 1962, page 247, 248; and "Chemistry of Organic Fluorine Compounds," 2nd (Revised) edition, Hudlicky, Ellis Horwood Ltd., Chichester, England, 1976, pages 214-216. The conversion of perfluorinated aliphatic monocarboxylic acids and salts thereof to aliphatic chlorides, bromides and iodides is known, for example, from U.S. Pat. No. 2,647,933; Hudlicky, supra, 1962, page 226; and Haszeldine, *J. Chem. Soc.*, 1951, 584.

It is an object of this invention to provide chlorodifluorovinyloxyperfluoroalkyleneoxyalkyl trifluoromethyl ketones and acyl fluorides; chlorodifluorovinyloxyperfluoroalkyleneoxyethylenes; substituted fluoroalkoxyperfluoroalkyleneoxyalkyl trifluoromethyl ketones and acyl fluorides; substituted fluoroalkoxyperfluoroalkyleneoxyethylenes; processes for their preparation and for the preparation of perfluorovinyloxyalkyleneoxyalkyl bromides; and copolymers of derivatives of the aforesaid vinyl compounds. Other objects will become apparent hereinafter.

DISCLOSURE OF INVENTION

For further comprehension of the invention, and of the objects and advantages thereof, reference may be made to the following description and to the appended claims in which the various novel features of the invention are more particularly set forth.

The invention herein resides in processes for preparing fluorinated compounds, and more specifically, fluorinated compounds which are of the formulas:

  (1)

  (2)

  (3)

  (4)

  (5)

wherein n is an integer and is 1 to 6, p is an integer and is 0 to 3, Q is $CF_2XCFX^1$ or $CFCl=CF$, X and $X^1$ are both Cl or X is F or OR and $X^1$ is H, and R is methyl, cyclohexyl, phenyl or alkyl of 2 to 6 carbon atoms optionally interrupted with ether oxygen.

The invention herein also resides in the fluorinated compounds of formulas 2 to 5, preferred embodiments of which include those wherein, in formulas 2 to 5, n is 1; in formula 2, X and $X^1$ are both Cl or X is $OCH_3$ and $X^1$ is H; and in formulas 4 and 5, p is 0 and X and $X^1$ are both Cl or X is $OCH_3$ and $X^1$ is H.

In summary of the processes of the invention, the compound of formula 1 is obtained by pyrolyzing the salt of the formula

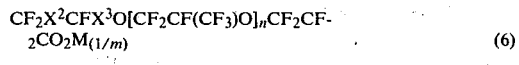  (6)

wherein M is an alkali or alkaline earth metal of valence m and $X^2$ and $X^3$ are both Br; the compound of formula 2 is obtained by pyrolyzing the compound of formula 6 wherein M is as previously defined, $X^2$ and $X^3$ are both Cl, or $X^2$ is F or OR, as previously defined, and $X^3$ is H. The compound of formula 3 is obtained by heating the compound of formula 2, wherein X and $X^1$ are both Cl, with magnesium or a mixture of zinc and zinc chloride. The compound of formula 4 is obtained by reacting either of the compounds of formulas 2 and 3 with hexafluoropropene oxide (HFPO); the compound of formula 5 is obtained by pyrolysis of the compound of formula 4.

The precursor of the salt of formula 6 is prepared by reacting the known ester of the formula

, wherein n is an integer and is 1 to 6 and $R^1$ is methyl or ethyl, with bromine, chlorine, hydrogen fluoride or an alkanol of the formula ROH wherein R is as defined above. Use of an aprotic solvent, such as tetraglyme, although not essential, may be desirable, particularly as the value of n increases. The reaction with bromine or chlorine is facilitated by cooling the reaction flask in ice and irradiating with UV light. The reaction with the alkanol of the formula ROH is carried out in the presence of a small amount of an alkoxide ROM' wherein R is as defined above and M' is an alkali metal cation. Methyl alcohol and ethyl alcohol are the preferred alcohols. An excess of alcohol is normally preferred. The addition of hydrogen fluoride across the double bond does not proceed readily, but may be accomplished by nucleophilic addition of fluoride ion by means of an alkali metal fluoride such as potassium fluoride in a proton-donating liquid such as formamide.

After the addition across the double bond of the ester has been completed, the resultant ester is converted to the alkali metal or alkaline earth metal salt of formula 6 by hydrolyzing with an alkali or alkaline earth metal hydroxide, preferably sodium hydroxide or potassium hydroxide, dissolved in water or, preferably, in methyl alcohol. Alternatively, the salt of formula 6 wherein $X^2$ is OR and $X^3$ is H can be prepared in one step from the aforesaid unsaturated ester by reaction with an alkanol ROH, wherein R is as defined above, in the presence of an alkali metal hydroxide, such as sodium hydroxide or potassium hydroxide, the hydroxide being present in slight molar excess with respect to the ester.

The salt, of formula 6, is isolated and pyrolyzed in a suitable aprotic solvent, such as a glyme (mono-, di-, tri or tetraethyleneglycol dimethyl ether), preferably tetraglyme, at a temperature of about 130° C. to about 300° C., preferably 170° C. to 230° C. Preferably, the solvent should be higher boiling than the pyrolysis reaction product, the compound of either formula 1 or formula 2.

Alternatively, although less desirably, the unhydrolyzed halogenated or alkanolated ester can be pyrolyzed in a suitable aprotic solvent, at the aforesaid temperatures, in the presence of a carbonate, phosphate, sulfite or sulfate salt of an alkali or alkaline earth metal, preferably sodium carbonate, trisodium phosphate or sodium sulfite, said unhydrolyzed halogenated or alkanolated ester being of the formula $$CF_2X^2CFX^3O[CF_2CF(CF_3)O]_nCF_2CF_2CO_2R^1$$

wherein n is an integer and is 1 to 6, $R^1$ is methyl or ethyl and $X^2$ and $X^3$ are both Br or Cl or $X^2$ is OR wherein R is methyl, cyclohexyl, phenyl or alkyl of 2 to 6 carbon atoms optionally interrupted with ether oxygen and $X^3$ is H. Such alkali or alkaline earth metal salts (catalysts) are not required or desirable when the alkali or alkaline earth metal salt of formula 6 is pyrolyzed.

It is important that all reactants and solvents used in the pyrolysis of the alkali or alkaline earth metal salt of formula 6 be moisture-free. The presence of water or other proton-bearing compounds during pyrolysis lowers the yield of the desired bromide of formula 1 or ketone of formula 2 by producing a hydrogen-capped by-product of the formula $$CF_2X^2CFX^3O[CF_2CF(CF_3)O]_nCF_2CF_2H$$

wherein n, $X^2$ and $X^3$ are as defined above.

Various methods of drying the alkali or alkaline earth metal salt of formula 6 can be used, including evaporative removal of water, azeotropic distillation of water with toluene, and neutralization in methanol solution followed by evaporative removal of methanol. In all these methods final drying in a vacuum oven is required to ensure complete removal of water or methanol. Neutralization in methanol is preferred because less foam is generated in the drying process, and the lower boiling point and lower heat of vaporization of methanol relative to water increases the drying rate.

Solvents used in the pyrolysis of the salt are dried by standard methods for drying organic liquids; distillation from sodium hydride is convenient.

As indicated above, the salt of formula 6 is an alkali or alkaline earth metal salt. Ammonium or tetraalkylammonium salts should be avoided, since their pyrolysis also leads to the formation of hydrogen-capped products or to the formation of alkyl esters.

Reaction pressure is not a critical variable for the pyrolysis of the salt of formula 6. Pressure above or below atmospheric pressure can be employed. Atmospheric or subatmospheric pressure is preferred, however, because of the comparative ease of recovering the distillable reaction products.

The pyrolysis of the salt of formula 6 wherein $X^2$ and $X^3$ are Br provides the bromo-functional perfluorovinyl ether of formula 1, along with a by-product of the formula $$CF_2BrCFBrO[CF_2CF(CF_3)O]_nCF_2CF_2Br$$

wherein n is as defined above, shown in Example 4. The by-product can be converted to the vinyl ether of formula 1 by heating in the presence of metallic zinc or magnesium, which selectively eliminates bromine from the 1,2-positions. Such an elimination of bromine from fluorinated 1,2-dibromoalkanes is known, for example, from Hudlicky, supra, 2nd (Revised) edition, pages 482, 483.

The formation of the vinyl ether of formula 1 by pyrolysis of the dibrominated salt of formula 6 is not only novel but unexpected. Pyrolysis of the dichlorinated salt of formula 6, under similar conditions, does not yield the chloride analog of formula 1, but rather the 1,2-dichloro-trifluoromethyl ketone of formula 2. Pyrolysis of the alkanolated salt of formula 6 also yields a trifluoromethyl ketone of formula 2 wherein X is OR and $X^1$ is H.

The vinyl ether of formula 1 can be copolymerized with fluorinated olefins, for example, tetrafluoroethylene, chlorotrifluoroethylene, vinylidene fluoride and perfluoroalkylvinyl ethers wherein the alkyl moiety contains 1 to 4 carbon atoms. The resulting copolymers, which contain pendant bromo groups, are curable to fluoroelastomers by means of peroxides and heat or by means of UV radiation.

Formation of the trifluoromethyl ketone of formula 2 by pyrolysis of the salt of formula 6, wherein $X^2$ and $X^3$ are Cl or $X^2$ is F or OR and $X^3$ is H, is accompanied by the loss of one mole of tetrafluoroethylene, one mole of carbon dioxide and one mole of sodium fluoride per mole of salt.

The trifluoromethyl ketone of formula 2 wherein X and $X^1$ are both Cl can be dechlorinated to the monochlorodifluorovinyl ether of formula 3 by heating in the presence of magnesium or a mixture of zinc and zinc chloride in an aprotic solvent such as diglyme.

The ketone of formula 2 where X and $X^1$ are both Cl or X is F or OR and $X^1$ is H, and the vinyl ether of formula 3, can be reacted with hexafluoropropene oxide (such as in Example 10) and the resultant adduct, of formula 4, can be pyrolyzed in the presence of a carbonate, phosphate, sulfite or sulfate salt of an alkali or alkaline earth metal, preferably sodium carbonate, trisodium phosphate or sodium sulfite, or after conversion to a salt by alkaline hydrolysis, to the copolymerizable vinyl ether monomer, of formula 5, by known methods, such as those disclosed in U.S. Pat. No. 3,274,239. The vinyl ether 5 can be copolymerized with fluorinated olefins such as, for example, tetrafluoroethylene, chlorotrifluoroethylene, vinylidene fluoride, and/or perfluoroalkylvinyl ethers wherein the alkyl moiety contains 1 to 4 carbon atoms, the fluorinated copolymers being moldable into shaped articles.

Copolymers prepared from the monomer of formula 5 wherein Q is $CF_2XCFX^1$, X is OR and $X^1$ is H can be further reacted by known methods to convert the pendant RO— group to another useful functional group, for example, an ester ($RO_2C$—) or acyl fluoride (FOC—) group. Copolymers containing these groups are, after hydrolysis, water-wettable and dyeable and possess ion-exchange properties. The formation of the ester can be carried out in 96% sulfuric acid at 0° C. to 10° C. by the process of Hudlicky, supra, 2nd (Revised) edition, page 271. The formation of the acyl fluoride can be carried out by reaction of the vinyl ether monomer or a copolymer thereof with a selected metal halide, such as antimony pentafluoride.

Copolymers prepared from the monomer of formula 5 wherein Q is CFCl=CF retain this terminal vinyl group and can be thermally cured to useful elastomers.

The ketone of formula 2 also can be reacted, under basic conditions, optionally in the presence of a solvent, with glycol half-esters to form 1,3-dioxolanes by known methods, such as disclosed in U.S. Pat. No. 2,925,424. By methods such as disclosed in U.S. Pat. Nos. 3,865,845 and 3,978,030, 1,3-dioxolanes can be converted to polymerizable fluorinated dioxoles.

In the following experiments and examples, parts are by weight unless otherwise indicated. Experiments 1 and 2 are representative of procedures for the preparation of intermediates, Examples 1 to 7 are representative of the invention.

EXPERIMENT 1

A. A 300 mL, 3-neck round-bottom flask fitted with a magnetic stirrer, pressure-equalizing dropping funnel and air-cooled condenser topped by a nitrogen bubbler, was flushed with nitrogen and charged with 117.5 g (0.28 mol) of methyl perfluoro-4,7-dioxa-5-methyl-8-nonenoate. Bromine was added with stirring and the reactant mixture was irradiated with a General Electric sunlamp. Bromine uptake was rapid. When a slight molar excess of bromine had been added, the flask was cooled in ice water. Excess bromine was destroyed by adding 20% aqueous sodium bisulfite solution. Two liquid layers were obtained. The lower layer was separated and washed with cold water; yield of crude product was 157.5 g. Distillation provided 147.3 g (91.0% yield) of colorless product; boiling point 86°–88° C./9 mm. Analyses using gas chromatography, infrared and $F^{19}$ NMR procedures confirmed that the product was methyl 8,9-dibromo-perfluoro-4,7-dioxa-5-methyl-nonanoate, $CF_2BrCFBrOCF_2CF(CF_3)OCF_2CF_2CO_2CH_3$.

B. 58.2 g of the ester prepared as in Part A, 50 mL of water and 4.0 g of sodium hydroxide were stirred at room temperature for 3 h in a 200 mL flask fitted with a magnetic stirrer and air-cooled condenser under nitrogen. The single liquid phase which was obtained was evaporated to dryness; yield of product was 54.8 g (92.9%). The $^{19}F$ NMR analysis of an aqueous solution of the product showed it to be sodium 8,9-dibromo-perfluoro-4,7-dioxa-5-methylnonanoate, $CF_2BrCFBrOCF_2CF(CF_3)OCF_2CF_2CO_2Na$, that is, the compound of formula 6 wherein $X^2$ and $X^3$ are both Br and n is one.

EXPERIMENT 2

A. A 200 mL flask fitted as described in Experiment 1A, except that the condenser was replaced by a Dry Ice-cooled trap, was charged with 77.9 g of methyl 4,7-dioxa-perfluoro-5-methyl-8-nonenoate and 100 mL of 1,1,2-trichloro-1,2,2-trifluoroethane. The flask was cooled in an ice bath, irradiated with a General Electric sunlamp, and chlorine was added. The reaction was exothermic and gas was evolved. Chlorine addition and irradiation were continued until gas evolution ceased. The reaction mixture, cooled in an ice bath, was treated with 75 mL of methanol, followed by 1.6 L of ice water. The lower layer which separated was removed and washed well with ice water. Fractional distillation of the lower layer resulted in 62.9 g (90.5% yield) of product, boiling point 77°–78° C./10 mm. Analyses by gas chromatography, infrared and $^{19}F$ NMR confirmed that the product was methyl 8,9-dichloro-perfluoro-4,7-dioxa-5-methylnonanoate), $CF_2ClCFClOCF_2CF(CF_3)OCF_2CF_2CO_2CH_3$.

B. 19.5 g of the ester product of Part A was hydrolyzed in 40 g of 50% aqueous sodium hydroxide and 40 g of water as described in Experiment 1B to obtain sodium 8,9-dichloroperfluoro-4,7-dioxa-5-methylnonanoate, $CF_2ClCFClOCF_2CF(CF_3)OCF_2CF_2CO_2Na$, that is, the compound of formula 6 wherein $X^2$ and $X^3$ are both Cl and n is one.

EXAMPLE 1

Fifty grams of methyl perfluoro(4,7-dioxa-5-methyl-8-nonenoate), $CF_2=CFOCF_2CF(CF_3)OCF_2CF_2CO_2CH_3$, was slowly added to a flask containing 50 mL of methanol and 4.8 g of sodium hydroxide. When the addition was complete, stirring was continued for 2 h. The excess methanol was evaporated and the semi-dry solid sodium salt was placed in a vacuum oven overnight.

Forty-six grams of the dried salt was added to a dry nitrogen-flushed flask along with 125 mL of tetraglyme. The mixture was warmed at a rate of about 5° C./min. At 195° C. decomposition of the salt began and product was distilled from the reaction mixture as it formed. Heating was continued to 205° C. for 10 min, at which time the decomposition was complete. The crude product was distilled to yield 6.1 g of pure material which was identified by its fluorine and proton nuclear magnetic resonance spectra, its infrared spectrum and its high resolution mass spectrum, all of which were consistent with the compound 1,1,1,3,3,5,6,6-octafluoro-5-H-2-oxo-4,7-dioxaoctane, $CH_3OCF_2CFHOCF_2C(O)CF_3$, that is, the compound of formula 2 wherein X is methoxy, $X^1$ is hydrogen and n is one.

EXAMPLE 2

Fifty grams of methyl perfluoro(4,7-dioxa-5-methyl-8-nonenoate) was placed in a flask and cooled to 0° C. Nineteen grams of bromine was added dropwise with stirring. The mixture was allowed to stir overnight and was then extracted with water, treated with activated carbon and filtered to yield a light orange liquid. The dibromide product, 59.2 g, was cooled in ice water and 4.07 g of sodium hydroxide dissolved in 25 mL of water was added dropwise. When all the sodium hydroxide was added, two layers formed. The mixture was shaken to yield a clear solution of neutral pH. The water was evaporated and the resultant salt was dried in a vacuum oven at 100° C. The salt was pyrolyzed in tetraglyme as described in Example 3. The crude product was distilled to yield 17.4 g of pure product which was identified from its fluorine nuclear magnetic resonance spectrum and its high resolution mass spectrum and shown to be 8-bromo-perfluoro-3,6-dioxa-5-methyl-1-octene, $CF_2=CFOCF_2CF(CF_3)OCF_2CF_2Br$, that is, the compound of formula 1 wherein n is one.

The reaction was repeated as described above, but at a two-fold increase in scale. In this case 35.5 g of the bromide product was obtained and 8.9 g of a second reaction product was isolated. This product, which was shown to be $CF_2BrCFBrOCF_2CF(CF_3)OCF_2CF_2Br$ by its fluorine nuclear magnetic resonance spectrum and its high resolution mass spectrum, could be converted to the principal product by reaction with zinc in diethyl ether.

EXAMPLE 3

In accordance with the procedure of Example 2, bromine, 30.6 g, was added dropwise to 112 g of $CF_2=CFO[CF_2CF(CF_3)O]_2CF_2CF_2COOCH_3$, prepared by known procedures. The ester thus produced was hydrolyzed and the resultant salt was pyrolyzed according to the procedure of Example 2. The isolated product, 33.1 g, was identified from its fluorine nuclear magnetic resonance spectrum and shown to be 11-bromo-perfluoro-5,8-dimethyl-3,6,9-trioxa-1-undecene, $CF_2=CFO[CF_2CF(CF_3)O]_2CF_2CF_2Br$, that is, the compound of formula 1 wherein n is two.

EXAMPLE 4

Fifty grams of methyl perfluoro(4,7-dioxa-5-methyl-8-nonenoate) was placed in a flask and cooled in ice water. Chlorine was bubbled into the reaction mixture until gas chromatographic analysis showed the starting material to be consumed. Excess chlorine was removed by bubbling nitrogen through the reaction mixture. The dichloride product which was formed was hydrolyzed to its sodium salt and pyrolyzed in tetraglyme by the procedure described for the dibromide in Example 2. Twelve grams of pure product was obtained. The product was identified by its infrared and fluorine nuclear magnetic resonance spectrum and shown to be 1,2-dichloro-perfluoro-3-oxa-5-oxohexane, $CF_2ClCFClOCF_2C(O)CF_3$, that is, the compound of formula 2 wherein X and $X^1$ are both Cl and n is one.

EXAMPLE 5

Five grams of the dichloroketone prepared in Example 4 was added to 10 mL of diglyme, 1.5 g of zinc metal and 0.1 g of zinc chloride. The mixture was heated to reflux for 2 h. After cooling, gas chromatographic analysis confirmed that all starting material had reacted. The major reaction product was isolated, 1.1 g, by distillation and identified from its infrared spectrum, fluorine nuclear magnetic resonance spectrum and high resolution mass spectrum, all of which were consistent with the structure 1-chloro-perfluoro-3-oxa-5-oxo-1-hexene, $CFCl=CFOCF_2C(O)CF_3$, that is, the compound of formula 3 wherein n is one.

EXAMPLE 6

36.2 g (0.08 mol) of $CF_3CFHOCF_2CF(CF_3)OCF_2CF_2CO_2Na$ and 80 mL of tetraglyme were stirred and heated in a 200 mL 3-neck flask fitted with a thermometer, stirrer and distillation column topped by a Dry Ice-cooled trap and nitrogen bubbler. The salt largely dissolved and reaction was noted in the temperature range 180° to 195°. 17.9 g of colorless distillate was obtained. Gas chromatography and IR analysis confirmed the presence of

(6.0 g, 28% yield), that is, the compound of formula 2 wherein X is F, $X^1$ is H and n is 1, and $CF_3CFHOCF_2CF(CF_3)OCF_2CF_2H$ (9.5 g, 31% yield).

EXAMPLE 7

1 g of potassium fluoride was added to a 50 mL round bottom flask fitted with a magnetic stirrer and Dry Ice condenser with gas inlet topped by a nitrogen bubbler. The flask was flamed out and cooled, then 10 mL of diglyme and 6.2 g (0.02 mol) of

prepared as in Example 4, were added and stirred until all the KF dissolved. 5 g (0.03L mol) of HFPO was then added. The reaction mixture was stirred at room temperature for 30 min; a clear, homogeneous yellow solution of the acyl fluoride $CF_2ClCFClOCF_2CF(CF_3)OCF(CF_3)COF$, that is, the compound of formula 4 wherein X and $X^1$ are both Cl, n is 1 and p is 0, in equilibrium with its KF adduct was obtained. 5 mL of methanol was added to the solution, resulting in an exothermic reaction. After stirring for 15 min at room temperature, 100 mL of water was added. A clear lower layer (10.5 g) was separated and analyzed by gas chromatography, IR and $^{19}F$ NMR spectroscopy. The principal component, b.p. 72°–74° at 10 mm, was identified as $CF_2ClCFClOCF_2CF(CF_3)OCF(CF_3)CO_2CH_3$.

BEST MODE FOR CARRYING OUT THE INVENTION

The best mode presently contemplated for carrying out the invention is demonstrated by Example 2 for the process of preparing the compound of formula 1, Example 4 for the compound of formula 2, Example 5 for the compound of formula 3, and Example 7 for the acyl fluoride of formula 4.

INDUSTRIAL APPLICABILITY

The fluorinated ketone of formula 2 can be converted, by reaction with HFPO, followed by pyrolysis of the resulting adduct, to a vinyl ether monomer from which copolymers can be prepared which, after hydrolysis, are water-wettable and dyeable and possess ion-exchange properties.

The fluorinated ketone of formula 3 can be converted to a copolymerizable monomer by the procedure used for the ketone of formula 2; copolymers derived therefrom are moldable and can be cured to fluoroelastomers.

Although I have illustrated and described the preferred embodiments of my invention, it is to be understood that I do not limit myself to the precise constructions herein disclosed and the right is reversed to all changes and modifications coming within the scope of the invention as defined in the appended claims.

I claim:
1. Compound of the formula

wherein n is an integer and is 1 to 6 and X and $X^1$ are both Cl or X is F or OR wherein R is methyl, alkyl of 2 to 6 carbon atoms, alkyl of 2 to 6 carbon atoms interrupted with ether oxygen, cyclohexyl or phenyl and $X^1$ is H.

2. Compound of claim 1 wherein n is 1 and X is $OCH_3$.

3. Compound of claim 1 wherein n is 1 and X and $X^1$ are both Cl.

4. Compound of the formula

wherein n is an integer and is 1 to 6.

5. Compound of claim 4 wherein n is 1.

* * * * *